United States Patent [19]

Bergli et al.

[11] Patent Number: 5,366,901
[45] Date of Patent: Nov. 22, 1994

[54] APPARATUS FOR ANALYZING CARBON PRODUCTS

[75] Inventors: Knut Bergli, Bødalen; Trygve Foosnaes, Årdalstangen; Tormod Naterstad, Asker, all of Norway

[73] Assignee: Norsk Hydro a.s., Oslo, Norway

[21] Appl. No.: 24,315

[22] Filed: Mar. 1, 1993

[30] Foreign Application Priority Data

Feb. 28, 1992 [NO] Norway ................................ 920790

[51] Int. Cl.⁵ .......................................... G01N 33/00
[52] U.S. Cl. .................... 436/133; 436/145; 436/147; 436/148; 436/149; 436/160; 422/68.1; 422/78; 422/82.01; 422/82.12; 422/82.13
[58] Field of Search ................ 436/133, 143, 145, 146, 436/147, 148, 149, 155, 160; 422/68.1, 78, 82.01, 82.02, 82.12, 82.13, 80, ; 73/865.5

[56] References Cited

U.S. PATENT DOCUMENTS

| | | | |
|---|---|---|---|
| 3,748,892 | 7/1973 | McKendree, Jr. et al. | 374/56 |
| 4,351,615 | 9/1982 | Vettori de Almeida Rodrigues | 374/56 |
| 4,522,787 | 6/1985 | O'Brien et al. | 422/78 |
| 4,522,788 | 6/1985 | Sitek et al. | 422/78 |
| 4,525,328 | 6/1985 | Bredeweg | 436/133 X |
| 4,643,977 | 2/1987 | Goleczka et al. | 436/145 X |
| 5,143,689 | 9/1992 | Hauser et al. | 374/55 |

OTHER PUBLICATIONS

P. J. Rhedey, Light Metals, 1982, pp. 713–725, "Carbon Reactivity and Aluminum Reduction Cell Anodes".
G. J. Houston et al., Light Metals, 1985, pp. 885–899, "Reactivity Testing of Anode Carbon Materials".
T. Müftüoglu et al., Light Metals, 1987, pp. 471–476, "Reactivity and Electrolytic Consumption of Anode Carbon With various Additives".

*Primary Examiner*—James C. Housel
*Assistant Examiner*—Maureen M. Wallenhorst
*Attorney, Agent, or Firm*—Wenderoth, Lind & Ponack

[57] ABSTRACT

An apparatus for the analysis of carbon products enables air reactivity, $CO_2$ reactivity, soot index and coefficient of thermal expansion of the carbon products to be determined in one analysis operation. The apparatus includes vertical and/or horizontal tube furnaces, each of which is provided with devices for weighing, temperature registration and/or registration dilation. Introduction of gas takes place via one end of each of the tube furnaces. Each of the furnaces is connected to a joint processing unit which checks the various instruments and registers the various instruments and registers and processes the analytical data.

8 Claims, 3 Drawing Sheets

APPARATUS FOR ANALYZING CARBON PRODUCTS

BACKGROUND OF THE INVENTION

The present invention relates to an apparatus for the analysis of granular coke, green and baked or burned carbon core samples.

It is the desire of every metal producer to have as much knowledge as possible about the properties of carbon-resistant parts of production equipment, such as anodes, cathodes and ramming paste. There are many factors which decide how a carbon product will react during a metal production process.

When the carbon product comes into contact with the air, in the way that the upper part of an anode usually does, the carbon will corrode. Another unfortunate process which occurs mainly on the underside of, for example, the anodes, is that some of the $CO_2$ gas from the primary reaction reacts with the carbon to form carbon monoxide. These two conditions are called air reactivity and $CO_2$ reactivity, respectively. Reactions with the air and $CO_2$ can lead to crumbling of the anode material which often has the result that operational problems occur with anode particles in the electrolyte. This is called sooting. The coefficient of thermal expansion (CTE) is a property of a carbon product which it is useful to know in metal production. Analysis of the coefficient of thermal expansion is called dilatometry.

Devices already exist to decide the above-mentioned properties of carbon products. However, such devices are capable of determining either the reactivity and the soot index or the coefficient of thermal expansion. In addition, the existing apparatuses are often large and imprecise and complicated and time-consuming to use. There has, therefore, long been a need for a more practical apparatus to measure these parameters of carbon products.

SUMMARY OF THE INVENTION

The present invention thus relates to an apparatus for the analysis of carbon products with regard to air reactivity, $CO_2$ reactivity, soot index and coefficient of thermal expansion. All these properties of a carbon product can be determined by using the apparatus of the present invention.

The apparatus of the present invention thus has a wide range of advantages compared with what was previously known in this field. Now only one apparatus is required by analyze a carbon product with regard to the above properties, whereas previously it was necessary to use at least two different apparatuses. This represents savings both of cost and time and also a saving in the number of operators required to operate the apparatus. In addition, the apparatus in accordance with the present invention has a compact design which means that it requires less space.

The apparatus of the invention comprises, among other things, a processing unit which controls various instruments and registers and processes analytical data. This has the result that the analyses which are carried out by this apparatus are very precise and rapid. For this reason, the apparatus is also easy to operate and, by the fact that the processing unit carries out necessary process control, the apparatus is both environmentally friendly and user friendly.

The apparatus for the analysis of carbon products in accordance with the present invention is characterized in that air reactivity, $CO_2$ reactivity, soot index and coefficient of thermal expansion are decided at the same time, i.e. during a single analysis operation, by means of vertical and/or horizontal tube furnaces, each of which is provided with devices for weighing, temperature registration and/or registration of dilation, and where gas is introduced via one end of the tube furnaces, with each of the furnaces being connected to a joint processing unit which controls the various instruments and processes the analytical data. The carbon samples which are to be analyzed for their reactivity and soot index are suspended via a sample holder from a weighing device, while the carbon samples which are to be analyzed for their coefficient of thermal expansion are connected to a differential transformer via a sample holder. The reactivity and soot index analyses can be carried out on granular coke and baked or burned carbon core samples. Dilatometry can be carried out on green and baked or burned carbon core samples.

BRIEF DESCRIPTION OF THE DRAWINGS

Other objects, features and advantages of the present invention will be apparent from the following detailed description taken with the accompanying drawings, wherein.

DETAILED DESCRIPTION OF THE INVENTION

Figure 1:
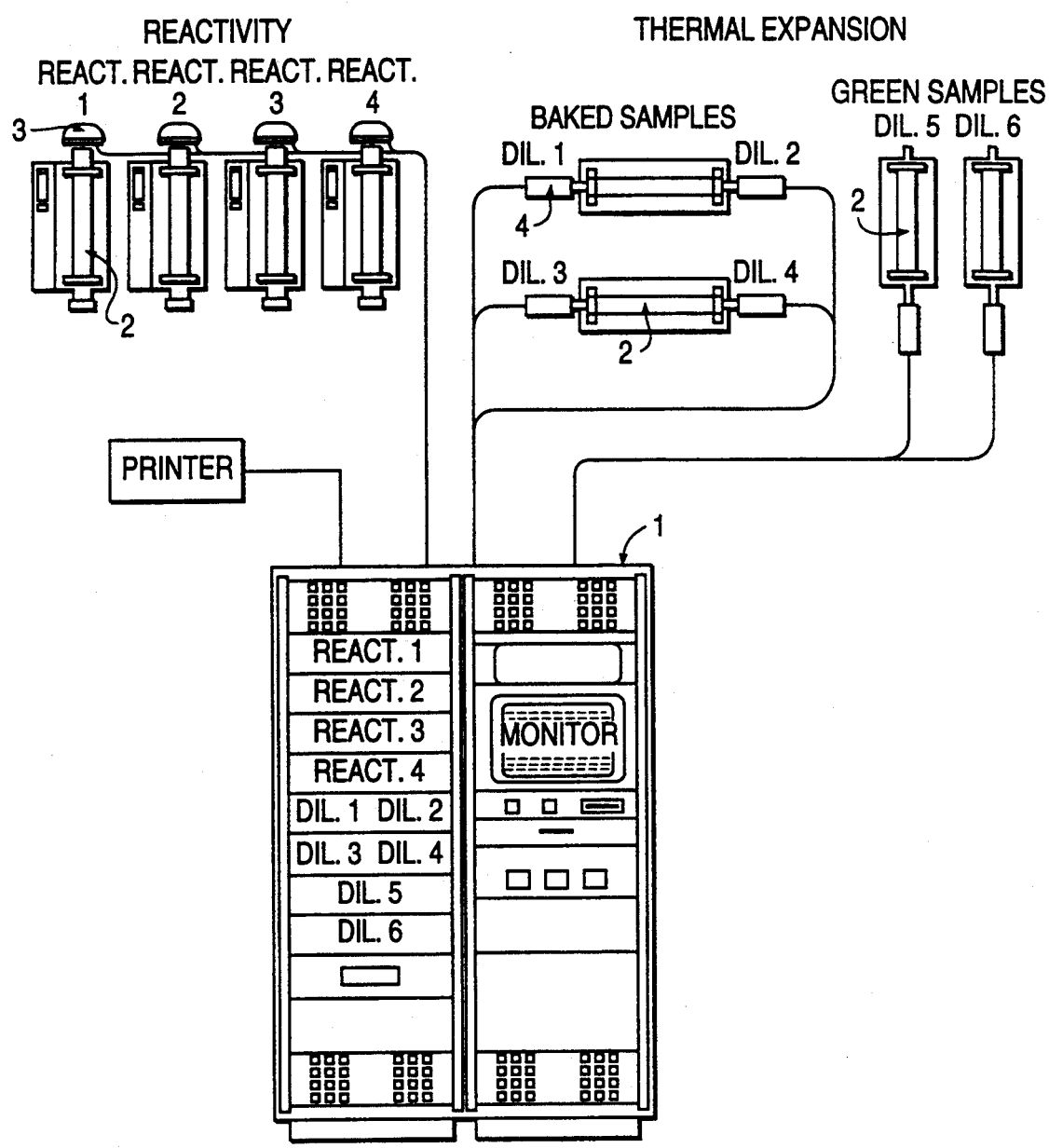
FIG. 1 is a schematic representation of an overall apparatus in accordance with the present invention.

An apparatus according to the present invention is shown in FIG. 1 and includes a processing unit 1, tube furnaces 2, weighing devices 3, and dilatometers 4. In principle there is no limit to how many carbon samples can be analyzed in parallel by connecting several tube furnaces to the computer equipment, i.e. processing unit 1.

Figure 2:
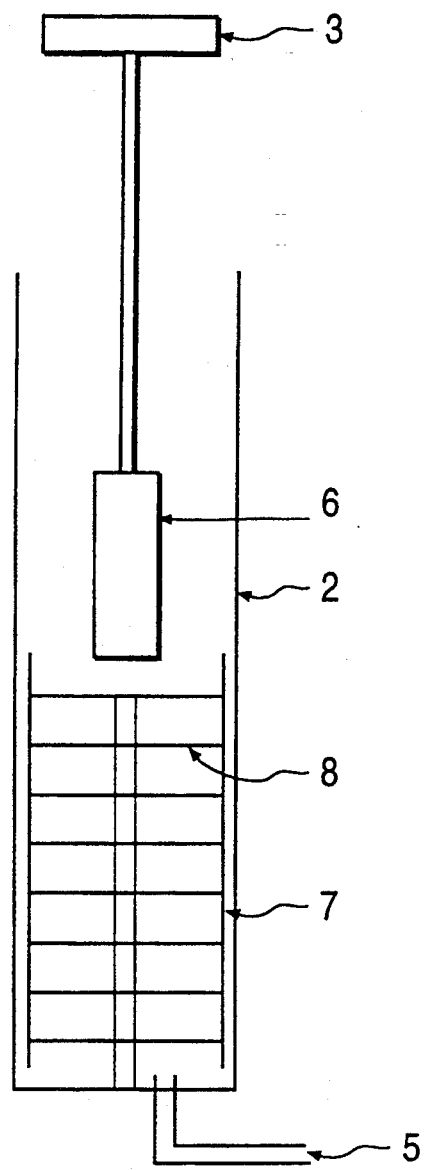
FIG. 2 is an enlarged schematic view of a portion of the apparatus employed for analyzing parameters of reactivity and soot index.

When determining air reactivity, $CO_2$ reactivity and the soot index, vertical tube furnaces with inlets for the introduction of gas are used. Sample holders for the respective carbon products are freely suspended from respective weighing devices and extend down into the respective tube furnaces. Each sample holder is provided with one or more thermocouples for registering the temperature of the respective carbon product. Such arrangement is shown in FIG. 2 wherein there are shown tube furnace 2, weighing device 3, inlet 5 for the introduction of gas into furnace 2, sample holder 6, radial radiation shield 7, and heating element 8.

Figure 3:
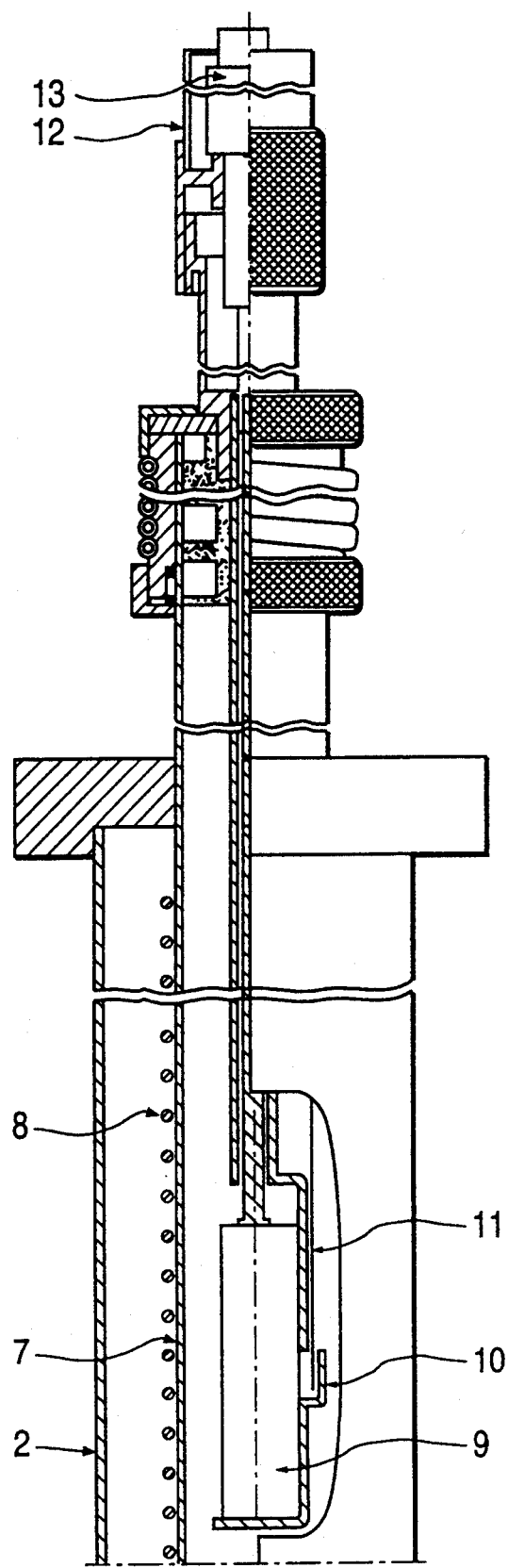
FIG. 3 is an enlarged schematic view of a portion of the apparatus employed for analyzing the parameter of coefficient of thermal expansion.

For dilatometry, vertical tube furnaces are used for green samples, whereas horizontal furnaces are used for baked or burned samples. Green samples must stand vertically during the analysis because the relatively soft material of these samples will fasten itself to the sample holder and give incorrect results if the furnace is horizontal. With horizontal tube furnaces, two baked or burned samples can be analyzed simultaneously in one furnace by placing one sample at each end of the furnace. Each tube furnace with an inlet for the introduction of gas thus forms a dilatometer including the sample holder for the carbon product which is placed slightly into the furnace. The sample holder, which is provided with a thermocouple, is connected to a differential transformer at the end of the tube furnace. FIG. 3 shows such an arrangement including tube furnace 2, radial radiation shield 7, heading element 8, carbon sample 9, sample holder 10, thermocouple 11, and housing 12 with a differential transformer 13.

The apparatus of the invention for the analysis of carbon products is applicable both for research and for routine tests during anode production.

The invention will be described further in the following.

Analysis of Reactivity and Soot Index

Analysis of reactivity and soot index of carbon samples is carried out at constant temperatures. Weight loss of the carbon sample due to gasification by air and carbon dioxide is measured continuously. In an equilibrium reaction, the loss of weight is proportional to time. The loss of weight as a function of time is an expression of the reaction speed which is thus called reactivity (air or $CO_2$ reactivity). The quantity of soot dust which is generated during such analysis is collected and weight and provides basis for calculation of a dimensionless parameter, namely the soot index.

A carbon sample is suspended by means of the sample holder 6 a slight distance down into the vertical tube 2 which is made of gold. In order that the weight loss may be followed continuously by the processing unit 1, the sample is suspended via the holder 6 from the weighing device 3. A thermocouple is also connected to the sample so that the temperature of the sample can be registered and checked. The temperature in the furnace and of the sample are regulated by the processing unit. Sample holders 6 used for the analysis of granular coke and for baked or burned carbon core samples are shaped differently, but both are shaped so that the thermocouple is in contact with the carbon product itself when the temperature is registered. This means that the temperature registration is very precise. Gas for the particular reactivity analysis is introduced into the furnace 2 from inlet 5 in the base of the furnace and is preheated to the reaction temperature as it passes radial radiation shield 7 within the furnace on the way towards the carbon sample. The introduction of the gas is also regulated by the processing unit 1.

The analysis of the carbon product for reactivity and soot index is carried out automatically by the processing unit 1 via dialogue boxes thereof. The processing unit controls switching from the introduction of one gas to the other automatically. During heating of the carbon sample inert atmosphere ($N_2$) is introduced. The processing unit closes a vale for the $N_2$ automatically and opens an air or $CO_2$ valve. When the particular reaction has been completed, the processing unit switches automatically back to $N_2$ and the sample is cooled down. Standard conditions during this analysis are:

Heating time: 60 minutes
Reaction time: 180 minutes
Cooling time: 30 minutes
Reaction temperature in $CO_2$: 960° C.
Reaction temperature in air: 525° C.

The flow of gas through the furnace is 100 Nl/h of $CO_2$ and 200 Nl/h of air. These reaction conditions may, however, be changed easily by the operator.

The weighing system in the apparatus has a reproducibility of 1 mg. The weight is registered on a continuous basis (every 20 seconds according to standard conditions). The high number of measurements, the good reproducibility of the weighing system and the advanced temperature control, which is within ±1° of the desired temperature, ensure high precision results of better than ±1%. The results of the analyses regarding reactivities and soot index are calculated by the processing unit 1.

In an apparatus which consists of eight tube furnaces, it is possible to analyze eight carbon samples in the course of 4.5 hours. The time required to prepare a carbon sample for analysis is 10 minutes. As mentioned above, the processing unit controls operation of the furnaces and performs analyses automatically. The time required for an operator to be able to prepare the samples, fasten the samples in the furnaces, remove the samples from the furnaces, collect the soot and read off the results for samples in eight furnaces is a total of 100 minutes.

Dilatometry

When the apparatus is used to determine dilatometry, the weighing device 3 to which a particular carbon sample is attached during the reactivity analysis is replaced by differential transformer 13. In addition, another sample holder 10, provided with a thermocouple 11 and connected to the differential transformer 13, is used. Differential transformer 13 makes it possible for volume changes and temperature of the sample to be registered in the processing unit 1, and the coefficient of thermal expansion of the sample can be calculated thereby.

The coefficient of thermal expansion (CTE) is expressed as the average increase in expansion of the carbon sample as a function of temperature. Analysis of the carbon product regarding the coefficient of thermal expansion is carried out by first introducing $N_2$ gas. The carbon product is heated up from room temperature to 800° C. at a standard heating rate of 10° per minute. The heating conditions easily can be changed by the operator if desired. The temperature and expansion are registered and plotted against one another. When the measurements have been completed, the furnace is cooled down to room temperature. During cooling from the maximum temperature to 400° C., the cooling speed is increased by adding $N_2$ under high pressure. When the temperature has dropped below 400° C. air under high pressure is used as a cooling medium. This entire process occurs automatically under the control of the processing unit 1. The coefficient of thermal expansion is calculated by the processing unit 1 on the basis of data which are stored during such operation.

This analysis lasts for 80 minutes plus the cooling time. The time which is required for an operator to prepare the samples, fasten the samples in the furnaces, remove the samples from the furnaces and read off the results for the samples for ten dilatometers is a total of 120 minutes.

We claim:

1. An analyzing apparatus for determining in a single analysis operation the parameters of air reactivity, $CO_2$-reactivity, soot index and coefficient of thermal expansion of carbon products, said apparatus comprising:

plural tube furnaces for receipt of respective carbon product samples to be analyzed, each said furnace having operatively associated therewith a device for determining temperature of a respective carbon product sample, and at least one said furnace having a device for determining weight of a respective carbon product sample and a device for collecting soot dust, and at least one other said furnace having a device for determining dilation of a carbon product sample, and each said furnace having at one end thereof an inlet having means for communicating with sources of air and carbon dioxide for the selective introduction thereinto of air or $CO_2$; and a processing unit operatively connected to all of said temperature determining, said weight determining, said soot dust collecting and said dilation determining devices to receive therefrom data representative of determinations made thereby for respective carbon product samples, and to, based on such data, automatically regulate operation of said furnaces, said devices and said inlets, and to analyze respective said parameters for the respective carbon product samples.

2. An apparatus as claimed in claim 1, wherein said at least one furnace which has a device for determining weight of a respective carbon product sample and a device for collecting soot dust is oriented vertically and has a lower end comprising said inlet and an upper end, and said weight determining device comprises a weighing member and a sample holder to support a carbon product sample, said sampler holder being suspended from said weighing member.

3. An apparatus as claimed in claim 2, wherein said temperature determining device of said at least one furnace which has a device for determining weight of a respective carbon product sample and a device for collecting soot dust comprises a thermocouple of said sample holder.

4. An apparatus as claimed in claim 1, wherein said at least one other furnace which has a device for determining dilation of a respective carbon product sample has therein a sample holder to support a carbon product sample, and said dilation determining device comprises a differential transformer positioned at an end of said at least one other furnace.

5. An apparatus as claimed in claim 4, wherein said at least one other furnace is oriented vertically.

6. An apparatus as claimed in claim 4, wherein said at least one other furnace is oriented horizontally.

7. An apparatus as claimed in claim 4, wherein said temperature determining device of said at least one other furnace which has a device for determining dilation of a respective carbon product sample comprises a thermocouple of said sample holder.

8. An apparatus as claimed in claim 1, wherein at least a first said furnace is oriented vertically and includes a respective said weight determining device and said soot dust collecting device, at least a second said furnace is oriented vertically and includes a respective said dilation determining device, and at least a third said furnace is oriented horizontally and includes a respective said dilation determining device.

* * * * *